United States Patent [19]

DeMarinis et al.

[11] 4,444,782
[45] Apr. 24, 1984

[54] 2(4-TERT.-BUTYL-2,6-DICHLOROPHENYL-IMINO)IMIDAZOLIDINE AND USE AS AN ANTI-HYPERTENSION AGENT

[75] Inventors: Robert M. DeMarinis, Ardmore; J. Paul Hieble, Philadelphia, both of Pa.

[73] Assignee: SmithKline Beckman Corporation, Philadelphia, Pa.

[21] Appl. No.: 452,676

[22] Filed: Dec. 23, 1982

[51] Int. Cl.³ .................. A61K 31/415; C07D 233/50
[52] U.S. Cl. ................................. 424/273 R; 548/315
[58] Field of Search ..................... 548/315; 424/273 R

[56] References Cited

U.S. PATENT DOCUMENTS 3,236,857 2/1966 Zeile et al. ........................ 424/273 R
3,454,701 7/1969 Zeile et al. ........................ 424/273 R

OTHER PUBLICATIONS

P. B. Timmermanns et al., J. Med. Chem. 20 1636 (1977).
J. P. Hieble et al., Arch. Pharmacol. 309 217 (1979).
A. DeJonge et al., J. Pharmacol. Exp. Ther., 222, 705 (1982).

Primary Examiner—Henry R. Jiles
Assistant Examiner—Kurt G. Briscoe
Attorney, Agent, or Firm—William H. Edgerton; Richard D. Foggio; Alan D. Lourie

[57] ABSTRACT 2-(4-tert.-Butyl-2,6-dichlorophenylimino)imidazolidine is a anti-hypertensive chemical compound which has unexpected biological properties compared to those of clonidine.

5 Claims, No Drawings

2(4-TERT.-BUTYL-2,6-DICHLOROPHENYL-IMINO)IMIDAZOLIDINE AND USE AS AN ANTI-HYPERTENSION AGENT

This invention relates to 2-(4-tert.-butyl-2,6-dichlorophenylimino)imidazolidine and its pharmaceutically acceptable salts which have useful anti-hypertensive activity.

BACKGROUND OF THE INVENTION

Among the scientific publications in the clonidine art, exemplary are P. B. Timmermanns et al., J. Med. Chem. 20 1636 (1977) and J. P. Hieble et al., Arch. Pharmacol. 309 217 (1979). Timmermanns is a detailed structure function analysis of this class of compounds in which he concludes at column 2, page 1643, that the para or 4-position "should be left unsubstituted".

Recently, A. DeJonge et al., J. Pharmacol. Exp. Ther., 222, 705 (1982) reported that a bulky substituent such as a chloro at the 5-position of a 2-phenyl iminoimidazolidine favors peripheral $\alpha_1$ receptor agonism over central receptor agonism. This publication is not a reference against the present invention.

The compound of the invention goes against the teaching of the art to give a compound whose qualitative biological activities differ significantly from those of clonidine. Clonidine (2-(2,6-dichlorophenylimino)-2-imidazolidine) is a potent anti-hypertensive, sedative agent which has led to extensive structure-activity examination of the series of phenylimino-2-imidazolidines.

U.S. Pat. Nos. 3,236,857 and 3,454,701 are examples of many publications in this art. Among the species specifically disclosed here is 2(4-tert.-butyl-2-chlorophenyl-imino)-2-imidazolidine, column 6, line 25 of U.S. Pat. No. 3,454,701. These two patents disclose no particular advantage of a 4-tert.-butyl pharmacophore. In fact, clonidine, itself, is mentioned as the most active and least toxic of the series, see column 10 of the latter patent.

It is believed that the compound of this invention as well as its unique biological spectrum are not taught in the prior art and that, in fact, the state of prior art would lead one skilled in the art away from preparing the compound.

DESCRIPTION OF THE INVENTION

The basic compound of this invention has the following structural formula:

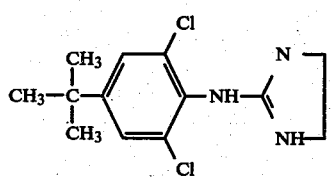

I

Chemically, the base compound of formula I is named 2-(4-tert.-butyl-2,6-dichlorophenylimino)imidazoline. From a structural viewpoint, it is the 4-tertiary butyl congener of the well-known antihypertensive agent, clonidine.

The compound of this invention has been found to have an unexpected specificity of action compared with that of clonidine. The latter product is known to act via alpha adrenergic stimulation. One troublesome side-effect of clonidine is due to its alpha agonist activity at presynaptic $\alpha_2$ receptor sites in the brain which lead, among other effects, to heavy sedation (see the Physician's Desk Reference pages 676–677, 36th, Ed., 1982). 2-(2-Chloro-4-ethylphenylimino)-imidazolidine is also described as a very strong sedative or sleep inducer (DS 1303-930, Derwent No. 15037X/09).

Since the early work on clonidine, at least two types of vascular alpha receptor sites have been identified. A postjunctional, or postsynaptic, $\alpha_1$ receptor was initially reported. It can be selectively stimulated by either phenylephrine or methoxamine and selectively blocked by prazosin. In the alpha test protocol in the isolated perfused rabbit ear artery described by J. P. Hieble et al., Arch. Pharmacol. 309, 218 (1979), the compound of this invention was eight times more potent as an agonist than was clonidine.

The second type of vascular alpha receptor site to be reported is located prejunctionally on sympathetic neurons and called $\alpha_2$ sites. The protocol employed for determining this activity is the isolated, superfused guinea pig left atrium described in the cited Hieble publication. In this protocol, clonidine was forty-six (46) times as active as the compound of this invention.

Recently, an additional postjunctional receptor subtype has been described which seems to resemble, in some respects, the prejunctional $\alpha_2$-receptor [P. B. Timmermans et al., J. Auton. Pharmacol. 1:171 (1981)].

Another test system to assay for vascular postjunctional $\alpha_2$ stimulation utilizes the dog saphenous vein. This activity may be called $\alpha_3$ stimulation. The protocol for this test is as follows:

Mongrel dogs of either sex are anesthetized with sodium pentobarbital (50 mg/kg, i.p.). After the dog is anesthetized, the saphenous vein is located and cleaned of connective tissue, a 2–4 cm. segment is tied at both ends and removed. The venous segment is placed in a dish of cold Krebs solution and additional cleaning is performed to remove as much non-vascular tissue as possible. Ring segments (3–4 mm.) are then cut from the vessel.

The vessel is mounted in a superfusion chamber as known to the art for the rabbit ear artery except that the insert holding the venous ring has two parallel 0.5 mm tungsten wires separated by 2 mm. The tissue is slipped over these parallel wires and the insert attached to the main block. A third tungsten wire is then inserted through the ring and attached to a force-displacement transducer.

An initial tension of 4 gm is placed on the tissue, with tension being adjusted until a stable resting tension of 2 gm. is produced. Concentration-effect curves are determined as described in the publication referred to above for the ear artery segment.

In this test, clonidine and the compound of this invention were about equipotent. Therefore, the compound of this invention had an $\alpha_2/\alpha_3$ ratio of 30 while the ratio for clonidine is 1. This indicates a more selective activity for the claimed compound at alpha receptor subtypes.

The data of these test results are summed up in the following table:

TABLE A

| | Alpha$_1$ Rabbit Ear Artery | Alpha$_2$ Guinea Pig Atrium | Alpha$_3$ Dog Saphenous Vein | $a_2/a_3$ Selectivity |
|---|---|---|---|---|
| (ED$_{50}$ nM) | | | | |
| COMPOUND I | 30 | 790 | 26 | 30 |
| CLONIDINE HYDROCHLORIDE | 290 | 17 | 16 | 1 |

When administered to animals, the compound of this invention demonstrated potent antihypertensive activity. In the normotensive rat model, the I.V. EC$_{30}$ for the reduction of blood pressure was 9.8 µg/kg.

In a standard assay for the sedative properties of a compound (potentiation of hexabarbitol induced sleep time) the ED$_{50}$ for potentiation of hexabarbitol induced sedation was 0.26 mg/kg. I.P.

In the same series of tests the EC$_{30}$ for the hypotensive effect of clonidine was 2.3 µg/kg I.V. while its ED$_{50}$ in the hexabarbitol sleep time assay was 0.0096 mg/kg, I.V.

Thus, clonidine is a far less selective agent and causes marked sedation at a dose almost 30 times lower than does the compound of this invention while it is only slightly more potent as a hypotensive agent. These in vivo results are in good correlation with the receptor specificity seen in vitro (Table A above). Here, clonidine shows very little specificity between pre- and postsynaptic receptor subtypes, while the compound of interest is 30-fold more selective for the postsynaptic receptor in vitro. The hypotensive activity of the iminoimidazolines has been ascribed by many workers to be due to activation of central postsynaptic alpha receptors, [W. Kobinger et al., Eur. J. Pharm., 40 311 (1976)] while sedation has been ascribed to stimulation of presynaptic alpha receptors [(A. Delini-Stula, et al., Naunyn-Schmiedeberg's Archs Pharmac., 307 115 (1979)]. This is in excellent agreement with the data we have generated both in vitro and in vivo.

In summary, the compound of this invention is an agent with surprising and unexpected selectivity on alpha receptor subtypes. This selectivity can be demonstrated in vitro and in vivo where it acts as a hypotensive agent devoid of the sedative side effects of other iminoimidazolines such as clonidine. Also, the compound of formula I has utility as a pharmacological tool whose activity in the outlined protocols, as well as others known to the art, serves as a standard with which other test compounds can be compared.

The pharmaceutical compositions used to produce alpha adrenoceptor stimulation and antihypertensive activity comprise a pharmaceutical carrier and, as the active ingredient, the compound of formula I. The active ingredient will be present in the compositions in an effective amount to produce alpha adrenoceptor stimulation as well as the resulting antihypertensive activity but not to have limiting side effects.

Preferably, the compositions contain a quantity of the active ingredient of formula I selected of the range of about 0.005 mg. to about 5 mg., advantageously from about 0.1 mg. to about 3 mg., per dosage unit.

The pharmaceutical carrier is, for example, a solid or a liquid. Exemplary of solid carriers are lactose, magnesium stearate, terra alba, sucrose, talc, stearic acid, gelatin, agar, pectin or acacia. The amount of solid carrier will vary widely, but preferably, will be from about 25 mg. to about 1 gm. Exemplary of liquid carriers are syrup, peanut oil, olive oil, sesame oil, propylene glycol, polyethylene glycol and water. The carrier or diluent may include a time delay material well known to the art such as, for example, glyceryl monostearate or glyceryl distearate, alone or admixed with a wax.

A wide variety of pharmaceutical forms can be employed. For example, the preparation may take the form of tablets, capsules, powders, troches, lozenges, syrups, suppositories, emulsions, sterile injectable liquids, liquid suspensions or liquid solutions, each calibrated for dosage unit quantities of the active ingredient.

The pharmaceutical compositions are prepared by conventional techniques involving procedures such as mixing, granulating and compressing or dissolving the ingredients as appropriate to the desired preparation.

Preferably, the compounds of Formula I are administered internally, orally, anally or parenterally, from 1-4 times daily in conventional dosage unit forms which are prepared by incorporating an appropriate dose of the compound with standard pharmaceutical carriers.

Preferably, the active ingredient of Formula I will be administered in a daily dosage regimen selected from about 0.1-15 mg., most preferably from about 2-5 mg. Advantageously, equal doses will be administered, preferably, two to three times per day.

In addition to its utility due to its antihypertensive activity, the compound of formula I and its salts are, as stated above, useful as analytical pharmacological agents as prototypal vascular alpha adrenoceptor stimulants.

The base compound of this invention is prepared conveniently by reacting 1-(4-tert.-butyl-2,6-dichlorophenyl-2-(2-aminoethyl)-thiourea under reaction conditions for ring closure which induce condensing the thioxo group with the primary amino group. An example of such conditions is reacting the thiourea in refluxing ethanol with mercuric oxide. The isolation of the base is carried out using methods known in the art. The acid addition salts of the base of formula I are prepared by reacting the base with at least one equivalent of the salt in an organic solvent. Useful acids are hydrochloric, hydrobromic, phosphoric, methanesulfonic, sulfamic, ethanedisulfonic or sulfuric acids.

The following example is illustrative of methods useful in preparing and using the compounds of this invention. All temperatures are in degrees Centigrade.

EXAMPLE 1

To a stirred flask containing 134 g. (1 m.) of tert.-butylbenzene was added dropwise a mixture of 192 g. of concentrated sulfuric acid and 89 g. of concentrated nitric acid. The temperature was maintained between 25°–35° by the intermittent use of an ice bath. The addition took about 1.5 hours, after which the mixture was stirred at room temperature for 5 hours and, then, allowed to stand at room temperature overnight.

The reaction mixture was warmed to almost 45° for 1 hour, poured onto ice and diluted with 200 ml. of ethyl ether. The organic layer was separated, washed with water, 5% sodium bicarbonate solution and brine, then dried and evaporated to give, as a pale yellow oil, 166 g. (88%) of 4-tert.-butylnitrobenzene.

Into 250 ml. of methanol was suspended 200 mg. of platinum oxide. To this was added 18.9 g. (0.1 ml.) of 4'-tert.-butylnitrobenzene and the reaction hydrogenated at 50 p.s.i. until no further hydrogen was absorbed. The catalyst was removed by filtration and the solvent evaporated. This procedure was repeated exactly as described on an additional 18.9 g. and, then, on a third 18.9 g. portion of starting material. The reaction mixtures were combined and worked up to give 44 g. (98%) of a brown oil, 4-tert.-butylaniline.

Into 50 ml. of pyridine was dissolved 12.0 g. of 4-tert.-butylaniline. The solution was cooled in a water bath and treated dropwise with 7.85 g., (0.10 m.) of acetyl chloride. When addition was complete, the semi-solid mixture was stirred at room temperature for 1 hour. The solution was poured into ice-water (400 ml.). The precipitate was removed by filtration and dissolved in methylene chloride which was dried and evaporated to give gummy reddish crystals. These were crystallized from charcoaled chloroform-hexane to give 7.8 g. of glistening, beige crystals (51%), m.p. 172–173.

Anal. Calcd for $C_{12}H_{12}NO$: C, 75.42; H, 9.02; N, 7.34. Found: C, 75.35; H, 8.96; N, 7.32.

Into 120 ml. of glacial acetic acid was suspended the acetanilide (19.1 g., 0.2 m.) and 500 mg of anhydrous ferric chloride. The reaction was stirred while chlorine was bubbled through for 3 hours. Periodic cooling kept the temperature at about room temperature for 2 hours. It was poured into 300 ml. of ice water and extracted twice with methylene chloride. The combined extracts were washed with water, cold 5% sodium hydroxide solution and saturated sodium chloride, dried and evaporated to give 27 g. of pale yellow crystals. Drying under pump vacuum for 2 hours gave 26 g. (88%) of pale yellow crystals of N-chloro-4-tert.-butyl-2,6-dichloroacetanilide.

Into 100 ml of Claisen's Alkali (alcoholic potassium hydroxide) was suspended 14.8 g. (50 mmol) of the chloroacetanilide. The mixture was refluxed overnight, cooled, poured into 400 ml. of ice-water, and extracted with two 200 ml. portions of methylene chloride which were then combined, washed with brine, dried and evaporated to give a dark reddish brown oil. This was eluted with hexane through a short silica gel column to give 5.9 g. (54%) of red oil, 4-tert.-butyl-2,6-dichloroaniline. Anal. Calcd. for $C_{10}H_{13}Cl_2N$: C, 55.07; H, 6.01; N, 6.42. Found C, 54,68; H, 6.05; N, 6.33

Into 150 ml. of toluene was dissolved 4.88 g. (22.5 mmol) of the amine, 3.00 g. (6.75 mmol) of magnesium oxide and 7.15 g. of thiophosgene. The mixture was stirred under reflux overnight. The insolubles were removed by filtration and the semi-solid residue (from evaporation of the solvent) was chromatographed quickly on silica gel, eluting with hexane, to give 3.8 g. (65%) of slightly off-white crystals, 4-tert.-butyl-2,6-dichlorophenylisothiocyanate, m.p. 63°–65°.

Into 200 ml. of toluene was dissolved 8.8 g. (147 mm.) of ethylene diamine. It was stirred at room temperature while the isothiocyanate (3.8 g., 14.7 mmol) in 20 ml. of toluene was added, dropwise. After addition was complete, thin layer chromatography showed complete consumption of starting material. The reaction was washed with water twice, then with saturated sodium chloride solution. A precipitate formed in the organic phase which was removed by filtration. It was taken up in methylene chloride, dried and evaporated to give 2.96 (63%) of white solid, m.p. 147–149. When the filtrate was reduced to about 10 ml., a second crop of 460 mg. of white crystals was isolated. Total yield 74%, overall, of 1-(4-tert.-butyl-2,6-dichlorophenyl)-2-(2-aminoethyl)thiourea.

Anal. Calcd. for $C_{13}H_{19}Cl_2N_3S$: C, 48.75; H, 6.00; N, 13.12; Found: C, 48.56; H, 6.00; N, 13.20.

Into 150 ml. of ethanol was dissolved 1.92 g. (6 mmol) of the thiourea. To this was added 5.2 g. (25 mmol) of yellow mercuric oxide. The mixture was stirred under reflux for 3 hours. The precipitate was removed by filtration through a filter aid. The solution was filtered again and evaporated to give 1.61 g. (95% crude) of slightly off-white crystals, m.p. 176°–182°. In some darkening at 160°. The compound was stirred with hexane. The solid was separated and dissolved in hot ether, then, filtered through filter aid to remove some precipitated impurities which formed a suspension. It was reduced in volume to about 10 ml. The product was crystallized by the addition of several volumes of pentane. The resulting crystals were removed by filtration and dried to give 1.2 g. (71%) of white needles, m.p. 212°–213.5°, with slight darkening, 2-(4-tert.-butyl-2,6-dichlorophenylamino)imidazolidine.

Anal. Calcd. for $C_{13}H_{17}Cl_2N_3$: C, 54.56; H, 5.99; N, 14.68; Found: C, 54.34; H, 5.99; N, 14.47.

The imidazolidine (50 mg.) is dissolved in ether and treated with hydrogen chloride gas to separate the hydrochloride salt.

A mixture of 2 mg. of the imidazolidine base and 400 mg. of lactose is filled into a hard gelatin capsule and administered orally three times daily to a hypertensive patient.

What is claimed is:

1. 2-(4-tert.-Butyl-2,6-dichlorophenylimino)imidazolidine or its pharmaceutically acceptable acid addition salts.

2. The compound of claim 1 being 2-(4-tert.-butyl-2,6-dichlorophenylimino)imidazolidine as the base.

3. The compound of claim 1 being 2-(4-tert.-butyl-2,6-dichlorophenylimino)imidazolidine hydrochloride.

4. A pharmaceutical composition having anti-hypertensive activity comprising a nontoxic, anti-hypertensively effective quantity of a compound of claim 1 combined with a pharmaceutical carrier in dosage unit form.

5. The method of inducing antihypertensive activity in a subject in need thereof without excess sedation comprising administering to said subject, orally, anally or parenterally, an antihypertensive, nontoxic quantity of a compound of claim 1.

* * * * *